(12) United States Patent
Xie et al.

(10) Patent No.: US 12,343,134 B2
(45) Date of Patent: Jul. 1, 2025

(54) QUANTITATIVE EVALUATION SYSTEM AND EVALUATION METHOD FOR COLOR OF HEMANGIOMA

(71) Applicants: GANNAN MEDICAL UNIVERSITY, Jiangxi (CN); JIANGXI UNIVERSITY OF CHINESE MEDICINE, Nanchang (CN)

(72) Inventors: Mingfeng Xie, Jiangxi (CN); Qian Liu, Jiangxi (CN); Xianyun Xu, Jiangxi (CN); Haijin Liu, Jiangxi (CN); Haijin Huang, Jiangxi (CN); Feng Chen, Jiangxi (CN); Linfu Li, Jiangxi (CN); Linshan Zeng, Jiangxi (CN); Yong Zeng, Jiangxi (CN); Jinlong Yan, Jiangxi (CN); Wei Peng, Jiangxi (CN)

(73) Assignees: JIANGXI UNIVERSITY OF CHINESE MEDICINE, Nanchang (CN); GANNAN MEDICAL UNIVERSITY, Jiangxi (CN)

( * ) Notice: Subject to any disclaimer, the term of this patent is extended or adjusted under 35 U.S.C. 154(b) by 383 days.

(21) Appl. No.: 17/906,748

(22) PCT Filed: Oct. 27, 2021

(86) PCT No.: PCT/CN2021/126742
§ 371 (c)(1),
(2) Date: Sep. 20, 2022

(87) PCT Pub. No.: WO2022/111195
PCT Pub. Date: Jun. 2, 2022

(65) Prior Publication Data
US 2023/0147076 A1    May 11, 2023

(30) Foreign Application Priority Data
Nov. 25, 2020 (CN) .......................... 202011338568.6

(51) Int. Cl.
*G06T 7/00* (2017.01)
*A61B 5/00* (2006.01)
(Continued)

(52) U.S. Cl.
CPC .......... *A61B 5/1032* (2013.01); *A61B 5/0077* (2013.01); *G06T 7/0012* (2013.01);
(Continued)

(58) Field of Classification Search
USPC ................ 358/1.1–3.29, 504–539, 480–485; 382/128–134, 153–225; 128/897–899,
(Continued)

(56) References Cited

U.S. PATENT DOCUMENTS

| 2010/0172562 | A1* | 7/2010 | Satoh | ................... G06T 7/0016 382/224 |
| 2012/0157800 | A1 | 6/2012 | Tschen | |
| 2021/0241027 | A1* | 8/2021 | Hu | ........................... G06T 7/11 |

FOREIGN PATENT DOCUMENTS

| CN | 108921179 A | 11/2018 |
| CN | 112446868 A | 3/2021 |

OTHER PUBLICATIONS

Vilenskii Maxim Alexeevich; Portable Device for Measurement of Chromophores in Skin and Method of Using Said Device; 2016 (Year: 2016).*
(Continued)

*Primary Examiner* — Marcellus J Augustin
(74) *Attorney, Agent, or Firm* — Chiesa Shahinian & Giantomasi PC (57) ABSTRACT

The present disclosure discloses a quantitative evaluation system and evaluation method for hemangioma. The evaluation system includes an image acquisition module, an image analysis module, a result evaluation module and a display module. The image acquisition module includes a
(Continued)

light source device, an imaging device and a storage device. The image analysis module includes a digital signal processor and digital analysis software. The digital signal processor divides pixel points of the hemangioma image into a tumor image and a tumor side image. The digital analysis software calculates comprehensive red, green, blue (RGB) values of the tumor image and the tumor side image. The result evaluation module includes a therapeutic evaluation coefficient, and the therapeutic evaluation coefficient=tumor comprehensive RGB value-tumor-side comprehensive RGB value.

20 Claims, 4 Drawing Sheets

(51) Int. Cl.
  *A61B 5/103*  (2006.01)
  *G06T 7/11*  (2017.01)
  *G06V 10/764*  (2022.01)
  *H04N 23/62*  (2023.01)
(52) U.S. Cl.
  CPC .............. *G06T 7/11* (2017.01); *G06V 10/764* (2022.01); *H04N 23/62* (2023.01); *A61B 2503/04* (2013.01); *G06T 2207/10024* (2013.01); *G06T 2207/30096* (2013.01)
(58) Field of Classification Search
  USPC ......... 128/920, 922–925; 600/300–312, 317, 600/340–342, 407–416, 473–477, 600/247–249, 921
  See application file for complete search history.

(56) References Cited

OTHER PUBLICATIONS

Sidorenko Ju.S.; Method for Diagnosing Skin Hemangioma in Children; 2000 (Year: 2000).*

International Search Report and Written Opinion mailed Dec. 21, 2021, in connection with International Patent Application No. PCT/CN2021/126742, filed Oct. 27, 2021, 9 pgs. (including translation).

Mingfeng et al., "The Preliminary Attempt to Evaluation of Treatment Effect of Superficial Infantile Hemangioma by Digital Image Analysis," 2020, Journal of Gannan Medical University, vol. 40, No. 3, 5 pgs. (including translation).

* cited by examiner

QUANTITATIVE EVALUATION SYSTEM AND EVALUATION METHOD FOR COLOR OF HEMANGIOMA

CROSS REFERENCE TO RELATED APPLICATION

This patent application is a National Stage under 35 U.S.C. 371 of International Patent Application No. PCT/CN2021/126742, filed Oct. 27, 2021, which claims the benefit and priority of Chinese Patent Application No. 202011338568.6, filed Nov. 25, 2020, the disclosures of all of which are incorporated by reference herein in their entirety as part of the present application.

TECHNICAL FIELD

The present disclosure relates to the field of medical technology, and particularly relates to a quantitative evaluation system and evaluation method for color of hemangioma.

BACKGROUND ART

Infantile Hemangioma (IH) is the most common benign tumor in infants, which is developed from the soft tissue of infants. The IH is a vascular tumor with unbalanced vascular homeostasis caused by abnormal regulation of vascular development and formation during the embryonic period. The incidence rate of the IH is 4%-10%, and the incidence rate is higher in premature infants and low birth weight infants (infants with birth weight <1000 g). The IH often appears on the face, limbs and other body surfaces, seriously affecting the infant patient's appearance, vision and mental health. The IH occurring in the respiratory tract and intracranial parts may cause respiratory obstruction, intracranial hemorrhage and other critical symptoms, and even cause death. The IH is one of the most common diseases that seriously endanger the physical and mental health of children. From a biological point of view, typical IH is divided into three phases: a proliferation phase, a plateau phase, and a remission phase. Natural course: lesions appear 1 to 2 weeks after birth, rapidly proliferate within 6 months, then gradually stop growing, and enter a spontaneous and slow remission phase, and this process may last for several years. In the proliferation phase of hemangioma, according to the degree of infiltration of the tumor of IH, the IH can be divided into a superficial type, a deep type and a mixed type. The superficial IH is often referred to as "strawberry hemangioma" according to its shape, and is a bright red mass with irregular protrusions on the surface and surrounded by normal skin tissue. After oral administration of propranolol, the state of an illness of sick children is relieved gradually. This process is manifested as: the tumor diameter decreases, the protrusion degree decreases, the local skin temperature changes, the tumor color changes, and the blood flow in the tumor cavity decreases.

At present, evaluation methods for the therapeutic effect of IH include: an Achauer percentile quartering method, a visual analog scoring method, an IH activity scoring method, an imaging auxiliary method (ultrasound, computed tomography (CT), magnetic resonance imaging (MRI)), a skin temperature method, and a measurement method of body fluids and biochemical indexes. However, there is no accurate, effective and objective evaluation method. The tumor color of IH can indirectly reflect the conditions of proliferation and remission, thereby becoming an important index for evaluating the state of an illness of sick children. Moreover, at present, for the evaluation of tumor color in sick children, clinicians' visual evaluation with a certain subjective color is commonly used, which causes great trouble to objectively and accurately evaluate the tumor color and reflect the state of an illness of sick children.

SUMMARY

In order to overcome the problems of inaccurate and inconvenient evaluation of hemangioma in the prior art, an objective of the present disclosure is to provide a quantitative evaluation system and evaluation method of hemangioma. The evaluation system has the advantages of high accuracy, convenience, practicality, and easy promotion.

In order to achieve the above objective, the present disclosure provides a quantitative evaluation system for color of hemangioma. The evaluation system includes an image acquisition module, an image analysis module, a result evaluation module and a display module;

the image acquisition module includes a light source device, an imaging device and a storage device; the imaging device acquires a hemangioma image, and the hemangioma image is stored in the storage device;

the image analysis module includes a digital signal processor and digital analysis software; the digital signal processor divides pixel points of the hemangioma image into a tumor image (31) and a tumor side image (32); the digital analysis software calculates comprehensive red, green, blue (RGB) values of the tumor image (31) and the tumor side image (32), and results are respectively recorded as a tumor comprehensive RGB value and a tumor-side comprehensive RGB value;

the result evaluation module includes a therapeutic evaluation coefficient, and the therapeutic evaluation coefficient=tumor comprehensive RGB value-tumor-side comprehensive RGB value; and the display module includes a display screen for displaying images and numerical values.

Preferably, the light source device includes a light source box and a light shield; and the light source box includes an infrared filter.

Preferably, a distance between the imaging device and an imaging object is fixed, and the distance is preferably 1 m.

Preferably, the digital signal processor classifies the pixel points of the hemangioma image into a red region and normal regions; the red region is the tumor image; by taking the largest diameter of a tumor as a diameter and a center point of the diameter as an original point, a plane rectangular coordinate system is established; four normal regions having a distance of 1 cm±0.5 mm from the outer sides of the edges of the tumor in four directions of the coordinate system and having an area of 1 cm²±0.5 cm² constitute the tumor side image; and the tumor side image is divided into four regions, namely a tumor side I, a tumor side II, a tumor side III and a tumor side IV.

Preferably, the digital analysis software converts and outputs the tumor image and the tumor side image to red, green and blue values and an RGB value, respectively recorded as R, G, B and comprehensive RGB values; the comprehensive RGB value of the tumor image is recorded as a tumor comprehensive RGB value; and an average value of the comprehensive RGB values of the four regions, namely the tumor side I, the tumor side II, the tumor side III and the tumor side IV, of the tumor side image is calculated and then recorded as a tumor-side comprehensive RGB value.

According to the second aspect of the present disclosure, the present disclosure provides a quantitative evaluation method for color of hemangioma. The quantitative evaluation method for color of hemangioma is performed in the quantitative evaluation system for color of hemangioma in the present disclosure, and the evaluation method includes the following steps:

S1: turning on the light source device and the imaging device to perform a system stability calibration process until the system stability reaches the standard;

S2: shooting a hemangioma image by the imaging device, and storing the hemangioma image in the storage device;

S3: dividing the hemangioma image into a tumor image (31) and a tumor side image (32) by the digital signal processor;

S4: calculating comprehensive RGB values of the tumor image (31) and the tumor side image (32) by the digital analysis software, and respectively recording results as a tumor comprehensive RGB value and a tumor-side comprehensive RGB value;

S5: calculating a therapeutic evaluation coefficient, where the therapeutic evaluation coefficient=tumor comprehensive RGB value-tumor-side comprehensive RGB value; and S6: displaying the hemangioma image, the tumor image (31), the tumor side image (32), the tumor comprehensive RGB value, the tumor-side comprehensive RGB value and the therapeutic evaluation coefficient by the display screen.

Preferably, in S1, the system stability calibration process includes the following steps:

a: placing a uniform white diffuse reflection plate in a measurement region, and adjusting an aperture size of a camera or a light source box to enable one component in RGB values of the shot image to reach 255;

b: placing a gray standard plate in the measurement region, and adjusting parameters of the camera to enable RGB three components of the output image to be 122, 122 and 121 respectively;

c: placing a black standard plate in the measurement region and/or covering a lens cap, and adjusting the parameters of the camera to enable the RGB three components of the output image to be 0 respectively; and d: placing a white standard plate in the measurement region, and adjusting the parameters of the camera to enable the RGB values of the output image to be 255 respectively.

Preferably, in S3, the division of the tumor side image includes the following steps: 1) selecting a center of the tumor image as an original point, and equally dividing the tumor image into four quadrants by a first quadrant axis, a second quadrant axis, a third quadrant axis and a fourth quadrant axis; and 2) selecting an image having a distance of 1±0.5 cm from the outer side of the tumor image on each of the quadrant axes and having an area of 1±0.5 cm² as a tumor side image.

Preferably, the tumor side image is divided into four regions, namely a tumor side I, a tumor side II, a tumor side III and a tumor side IV.

Preferably, in S3, the tumor-side comprehensive RGB value is an average value of the comprehensive RGB values of the four regions, namely the tumor side I, the tumor side II, the tumor side III and the tumor side IV, of the tumor side image.

Compared with the visual measurement in the prior art, the quantitative evaluation system and method for hemangioma provided by the present disclosure are more accurate and effective, are convenient and practical, and have extremely high promotion value.

By objectively quantifying the color depth of the tumor color, the quantitative evaluation system and evaluation method for color of hemangioma provided by the present disclosure have the advantages of more accurately reflecting the state of an illness of sick children and guiding doctors to treat.

DESCRIPTION OF REFERENCE NUMERALS

31—tumor image;
311—first quadrant axis;
312—second quadrant axis;
313—third quadrant axis;
314—fourth quadrant axis;
32—tumor side image;
321—tumor side I;
322—tumor side II;
323—tumor side III;
324—tumor side IV.

DETAILED DESCRIPTION OF THE EMBODIMENTS

The specific embodiments of the present disclosure will be described in detail below with reference to the accompanying drawings. It should be understood that the embodiments described herein are merely intended to illustrate and interpret the present disclosure, rather than to limit the present disclosure.

As mentioned above, the present disclosure provides a quantitative evaluation system for color of hemangioma. The evaluation system includes an image acquisition module, an image analysis module, a result evaluation module and a display module. The image acquisition module includes a light source device, an imaging device and a storage device. The imaging device acquires a hemangioma image, and the hemangioma image is stored in the storage device. The image analysis module includes a digital signal processor and digital analysis software. The digital signal processor divides pixel points of the hemangioma image into a tumor image 31 and a tumor side image 32. The digital analysis software calculates comprehensive RGB values of the tumor image 31 and the tumor side image 32, and results are respectively recorded as a tumor comprehensive RGB value and a tumor-side comprehensive RGB value. The result evaluation module includes a therapeutic evaluation coefficient, and the therapeutic evaluation coefficient=tumor comprehensive RGB value-tumor-side comprehensive RGB value. The display module includes a display screen for displaying images and numerical values. By objectively quantifying the color depth of the tumor color, the abovementioned scheme of the present disclosure has the advantages of more accurately reflecting the state of an illness of sick children and guiding doctors to treat.

Figure 1:
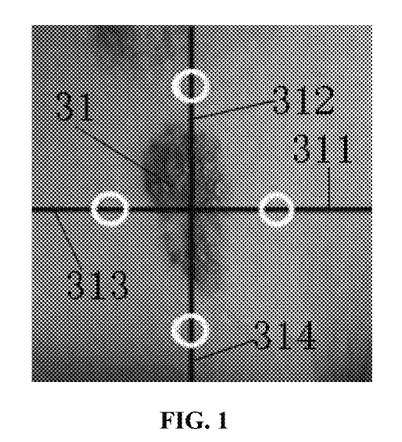
FIG. 1 is a schematic diagram of quadrant axes of a tumor side image divided by an image analysis module provided according to a preferred embodiment of the present disclosure.
Figure 2:
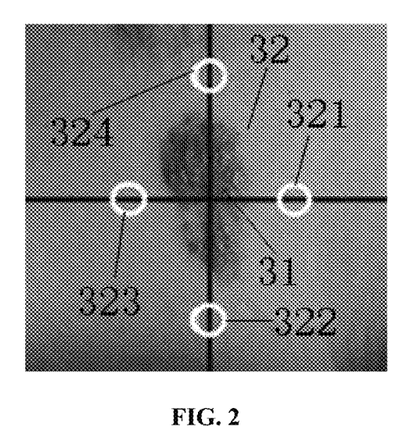
FIG. 2 is a schematic diagram of a tumor side image divided by an image analysis module provided according to a preferred embodiment of the present disclosure.
Figure 3:
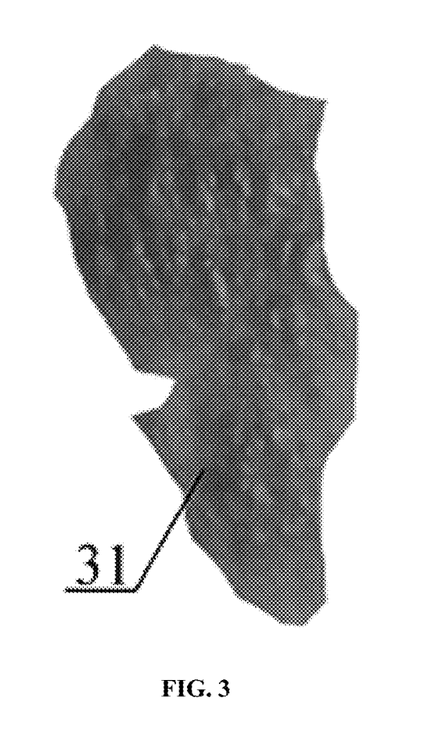
FIG. 3 is a tumor image divided by an image analysis module provided according to a preferred embodiment of the present disclosure.

Referring to FIG. 1 to FIG. 3, the present disclosure provides a quantitative evaluation system for color of hemangioma. The evaluation system includes an image acquisition module, an image analysis module, a result evaluation module and a display module.

According to the present disclosure, the image acquisition module includes a light source device, an imaging device and a storage device. The imaging device acquires a hemangioma image, and the hemangioma image is stored in the storage device.

In a preferred embodiment of the present disclosure, the light source device uses a P120 light source box and a PHILIPS-TLD-36W/865 strip-shaped three-primary fluorescent lamp, the model of a lamp holder of the light source is G13, a color rendering index is 85, and the light with a color temperature of 6500 K can be emitted. The light source can be used as a full-spectrum light source to ensure the spatial uniformity of the light, so that the light can be uniformly emitted to the tumor site to be shot.

In a preferred embodiment of the present disclosure, the imaging device uses an Olympus digital camera with a model of D33235, a total pixel of 10 million and an effective pixel of 9.3 million, an M.Zuiko professional lens is used, and a sensor is a charge coupled device (CCD) with a size of 17.4 mm*13.0 mm.

According to the present disclosure, the storage device is any one or more of a network cloud disk, a semiconductor memory, a magnetic surface memory and an optical surface memory.

In a preferred embodiment of the present disclosure, the light source device includes a light source box and a light shield for shielding external light, thereby eliminating the influence of ambient light on a measurement system.

In a preferred embodiment of the present disclosure, the light source box includes an infrared filter which can effectively reduce the temperature of the output light, thereby reducing the influence of the self-heating temperature of the light on the skin color, and ensuring that the acquired image can accurately reflect the state of an illness of sick children.

In a preferred embodiment of the present disclosure, a distance between the imaging device and an imaging object is fixed, which is 1 m, thereby ensuring that the imaging object can be clearly imaged.

In a preferred embodiment of the present disclosure, the imaging device is mounted on a bracket with an adjustable direction, so that the imaging device is more convenient to use.

According to the present disclosure, the image analysis module includes a digital signal processor and digital analysis software.

According to a preferred embodiment of the present disclosure, the digital signal processor and the digital analysis software are ImageJ and/or Photoshop.

The digital signal processor divides pixel points of the hemangioma image into a tumor image 31 and a tumor side image 32. The digital analysis software calculates comprehensive RGB values of the tumor image 31 and the tumor side image 32, and results are respectively recorded as a tumor comprehensive RGB value and a tumor-side comprehensive RGB value.

In a preferred embodiment of the present disclosure, the digital signal processor classifies the pixel points of the hemangioma image into a red region and normal regions; the red region is the tumor image 31; by taking the largest diameter of a tumor as a diameter and a center point of the diameter as an original point, a plane rectangular coordinate system is established; four normal regions having a distance of 1 cm from the outer sides of the edges of the tumor in four directions of the coordinate system and having an area of 1 $cm^2$ constitute the tumor side image 32; and the tumor side image 32 is divided into four regions, namely a tumor side I 321, a tumor side II 322, a tumor side III 323 and a tumor side IV 324.

In a preferred embodiment of the present disclosure, the digital analysis software converts and outputs the tumor image 31 and the tumor side image 32 to red, green and blue values and an RGB value, respectively recorded as R, G, B and comprehensive RGB values; the comprehensive RGB value of the tumor image 31 is recorded as a tumor comprehensive RGB value; and an average value of the comprehensive RGB values of the four regions, namely the tumor side I 321, the tumor side II 322, the tumor side III 323 and the tumor side IV 324, of the tumor side image 32 is calculated and then recorded as a tumor-side comprehensive RGB value. An average comprehensive RGB value of the four tumor side regions is taken as the tumor-side comprehensive RGB value to reduce system errors.

According to the present disclosure, the result evaluation module includes a therapeutic evaluation coefficient, and the therapeutic evaluation coefficient=tumor comprehensive RGB value-tumor-side comprehensive RGB value. The influence of the individual skin color difference of sick children on the result is reduced by the therapeutic evaluation coefficient, thereby more accurately reflecting the therapeutic effect on sick children.

The display screen may be a liquid crystal display screen.

Figure 4:
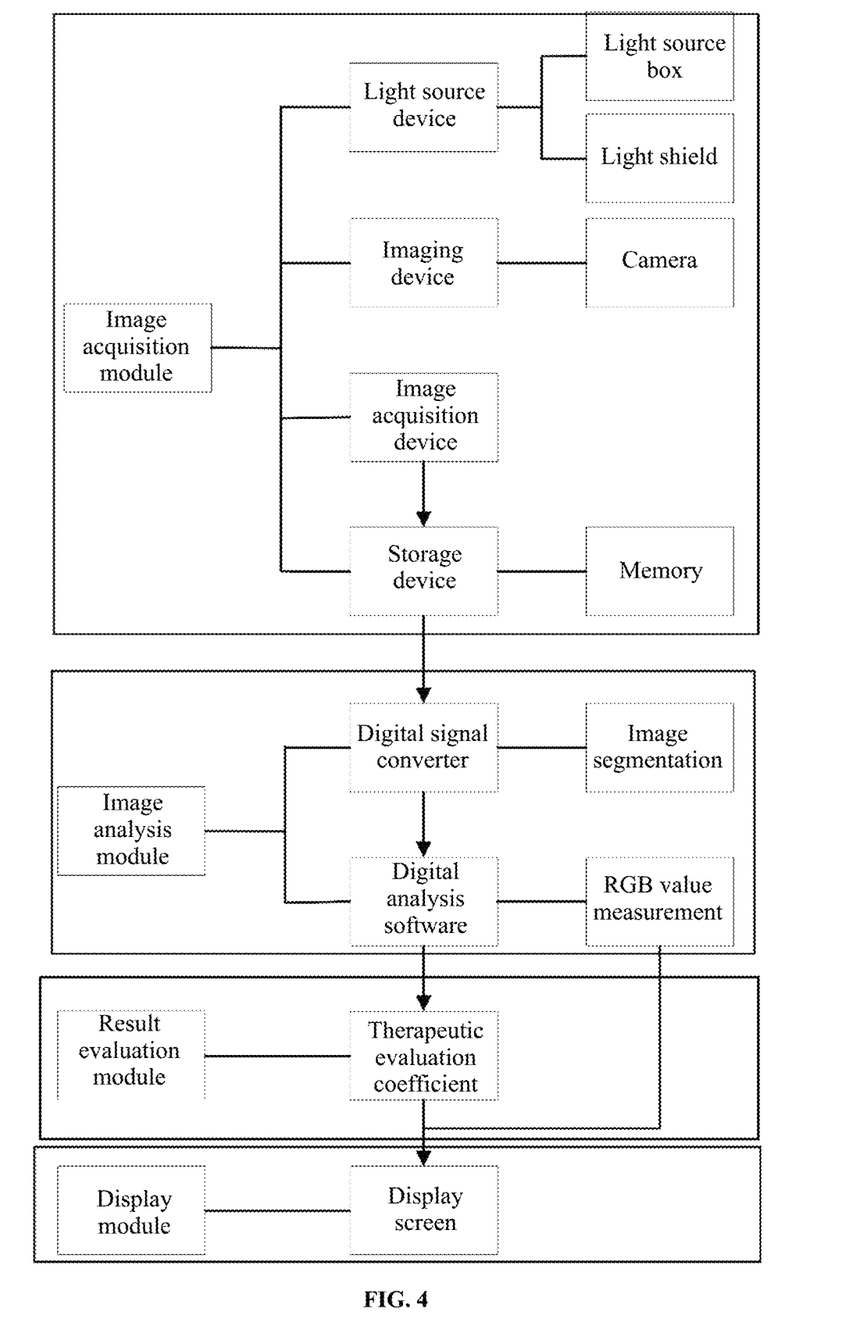
FIG. 4 is a schematic structural diagram of a quantitative evaluation system for hemangioma in the present disclosure.
Figure 5:
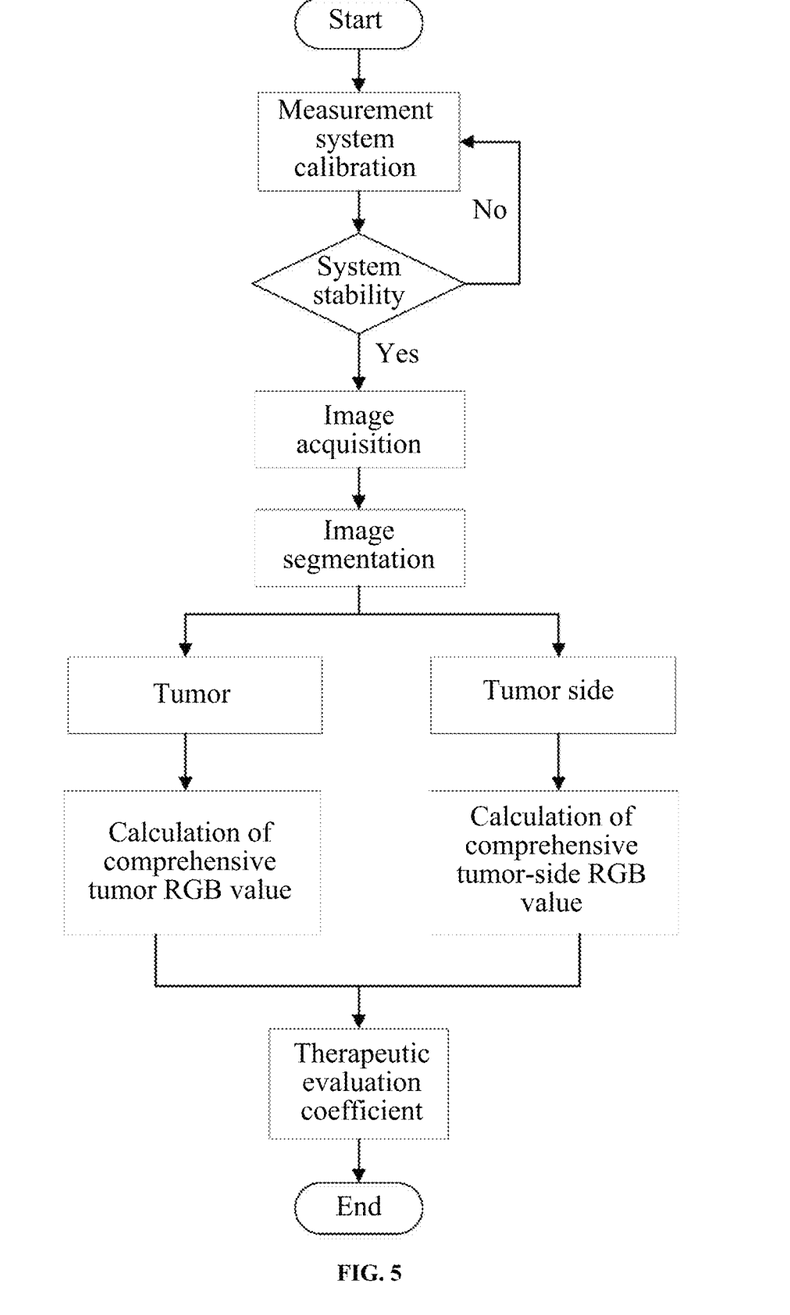
FIG. 5 is a schematic diagram of a quantitative evaluation method for hemangioma in the present disclosure.

Referring to FIG. 4, another aspect of the present disclosure provides a quantitative evaluation method for color of hemangioma. The evaluation method is performed in the quantitative evaluation system for hemangioma. The evaluation method includes the following steps:

S1: the light source device and the imaging device are turned on to perform a system stability calibration process until the system stability reaches the standard;

S2: a hemangioma image is shot by the imaging device, and the hemangioma image is stored in the storage device;

S3: the hemangioma image is divided into a tumor image 31 and a tumor side image 32 by the digital signal processor;

S4: comprehensive RGB values of the tumor image 31 and the tumor side image 32 are calculated by the digital analysis software, and results are respectively recorded as a tumor comprehensive RGB value and a tumor-side comprehensive RGB value;

S5: a therapeutic evaluation coefficient is calculated, where the therapeutic evaluation coefficient=tumor comprehensive RGB value-tumor-side comprehensive RGB value; and S6: the hemangioma image, the tumor image 31, the tumor side image 32, the tumor comprehensive RGB value, the tumor-side comprehensive RGB value and the therapeutic evaluation coefficient are displayed by the display screen for reference, evaluation and guidance of treatment by doctors.

In a preferred embodiment of the present disclosure, the stability of a measurement system is critical to the acquisition of high-quality images. The stability of the measurement system is affected by the unstable light output of a light source, the spatial unevenness of the light, the change of the spectral response characteristics of a CCD, the noise of a photoelectric conversion device, etc. In order to ensure the stability of the measurement system, the system stability calibration process includes the following steps:

a: a uniform white diffuse reflection plate is placed in a measurement region, and an aperture size of a camera or a light source box is adjusted to enable one component in RGB values of the shot image to reach 255;

b: a gray standard plate is placed in the measurement region, and parameters of the camera are adjusted to enable RGB three components of the output image to be 122, 122 and 121 respectively;

c: a black standard plate is placed in the measurement region and/or a lens cap is covered, and the parameters of the camera are adjusted to enable the RGB three components of the output image to be 0 respectively; and d: a white standard plate is placed in the measurement region, and the parameters of the camera are adjusted to enable the RGB values of the output image to be 255 respectively.

In a preferred embodiment of the present disclosure, in S3, the division of the tumor side image 32 includes the following steps:

1) a center of the tumor image 31 is selected as an original point, and the tumor image is equally divided into four quadrants by a first quadrant axis 311, a second quadrant axis 312, a third quadrant axis 313 and a fourth quadrant axis 314; and 2) an image having a distance of 1 cm from the outer side of the tumor image 31 on each of the quadrant axes and having an area of 1 cm² as a tumor side image 32.

In a preferred embodiment of the present disclosure, the tumor side image 32 is divided into four regions, namely a tumor side I 321, a tumor side II 322, a tumor side III 323 and a tumor side IV 324.

In a preferred embodiment of the present disclosure, in S3, the tumor-side comprehensive RGB value is an average value of the comprehensive RGB values of the four regions, namely the tumor side I 321, the tumor side II 322, the tumor side III 323 and the tumor side IV 324, of the tumor side image 32, so as to reduce system errors.

EMBODIMENT

S1: A quantitative evaluation system for color of hemangioma is mounted: a P120 light source box and a PHILIPS-TLD-36W/865 strip-shaped three-primary fluorescent lamp are used (the model of a lamp holder of a light source is G13, a color rendering index is 85, and the light with a color temperature of 6500 K can be emitted); an Olympus digital camera with a model of D33235, a total pixel of 10 million and an effective pixel of 9.3 million is used, an M.Zuiko professional lens is used, and a sensor is a CCD with a size of 17.4 mm*13.0 mm; a distance between the imaging device and an imaging object is fixed, which is 1 m; and a network cloud disk and a computer system are connected, and a digital signal processor Image J and digital analysis software Photoshop are turned on.

S2: System stability calibration is performed:

a: a uniform white diffuse reflection plate is placed in a measurement region, and an aperture size of a camera or a light source box is adjusted to enable one component in RGB values of the shot image to reach 255;

b: a gray standard plate is placed in the measurement region, and parameters of the camera are adjusted to enable RGB three components of the output image to be 122, 122 and 121 respectively;

c: a black standard plate is placed in the measurement region, and the parameters of the camera are adjusted to enable the RGB three components of the output image to be 0 respectively; and d: a white standard plate is placed in the measurement region, and the parameters of the camera are adjusted to enable the RGB values of the output image to be 255 respectively.

S3: The quantitative evaluation system for color of hemangioma is used for shooting and analyzing hemangioma of infant patients to obtain a tumor comprehensive RGB value, a tumor-side comprehensive RGB value and a therapeutic evaluation coefficient.

A total of 218 infant patients with superficial infantile hemangioma participated in this study, where 6 infant patients withdrew on their own, 5 infant patients were excluded due to too few follow-up times (less than 4 times) and were no longer included in this study, and finally, a total of 207 cases were included in this study. The clinical information (general information of infant patients) of this study are shown in Table 1.

TABLE 1

| General information of infant patients | |
|---|---|
| Item | |
| Age/month | 3.48 ± 1.96 |
| Male | 68 |
| Female | 139 |
| Average age at first consultation/month | 3.48 ± 1.96 |
| Average treatment time/month | 3.52 ± 1.82 |
| Tumor site: head and neck | 61 |
| Tumor site: limbs | 63 |
| Tumor site: body | 75 |
| Tumor site: perineum | 8 |

The quantitative evaluation system for color of hemangioma provided by the present disclosure and the evaluation scheme of the present disclosure were used for quantitative evaluation of tumors of infant patients. Measurement results are shown in Table 2.

TABLE 2

Tumor comprehensive RGB value, tumor-side comprehensive RGB value and therapeutic evaluation coefficient of sick children before and after treatment:

| Treatmen ttime period | 0 month of treatment | 1 month of treatment | 2 months of treatment | End of treatment |
|---|---|---|---|---|
| Tumor comprehensive RGB value | 90.14 ± 29.35 | 103.40 ± 31.77 | 112.68 ± 31.98 | 131.42 ± 33.93 |

TABLE 2-continued

Tumor comprehensive RGB value, tumor-side comprehensive RGB value and
therapeutic evaluation coefficient of sick children before and after treatment:

| Treatmen ttime period | 0 month of treatment | 1 month of treatment | 2 months of treatment | End of treatment |
|---|---|---|---|---|
| Tumor-side comprehensive RGB value | 146.93 ± 39.57 | 143.66 ± 35.92 | 141.07 ± 34.22 | 144.93 ± 36.40 |
| Therapeutic evaluation coefficient | −56.79 ± 22.07 | −40.21 ± 14.94 | −28.70 ± 12.72 | −13.17 ± 6.44 |

The results in Table 2 were analyzed by variance, where F=438.847, p<0.01. The variance results showed that there were significant differences in the therapeutic evaluation coefficients at different treatment times of sick children. The quantitative evaluation system for color of hemangioma in the present disclosure can objectively analyze the tumor color of infant patients to prompt the state of an illness of infant patients. Clinicians grouped the tumors of sick children according to growth states, and analyzed and found that there were significant differences in the therapeutic evaluation coefficients between the proliferation phase and the plateau phase, the proliferation phase and the remission phase, and the plateau phase and the remission phase of sick children.

The preferred embodiments of the present disclosure are described in detail with reference to the accompanying drawings and embodiments, but the present disclosure is not limited thereto. Within the scope of the technical concept of the present disclosure, a variety of simple modifications can be made to the technical solution of the present disclosure, including the combination of each specific technical feature in any suitable manner. In order to avoid unnecessary repetition, the present disclosure will not describe various possible combinations. However, these simple modifications and combinations should also be regarded as the contents disclosed in the present disclosure, and all belong to the protection scope of the present disclosure.

What is claimed is:

1. A quantitative evaluation system for hemangioma color, wherein the evaluation system comprises an image acquisition module, an image analysis module, a result evaluation module and a display module;

the image acquisition module comprises a light source device, an imaging device and a storage device; the imaging device acquires a hemangioma image, and the hemangioma image is stored in the storage device;

the image analysis module comprises a digital signal processor and digital analysis software; the digital signal processor divides pixel points of the hemangioma image into a tumor image and a tumor side image; the digital analysis software calculates comprehensive red, green, blue (RGB) values of the tumor image and the tumor side image, and results are respectively recorded as a tumor comprehensive RGB value and a tumor-side comprehensive RGB value;

the result evaluation module comprises a therapeutic evaluation coefficient; the therapeutic evaluation coefficient=tumor comprehensive RGB value−tumor-side comprehensive RGB value; and the display module comprises a display screen for displaying images and numerical values.

2. The quantitative evaluation system according to claim 1, wherein the light source device comprises a light source box and a light shield; and the light source box comprises an infrared filter.

3. The quantitative system according to claim 1, wherein a distance between the imaging device and an imaging object is fixed.

4. The quantitative system according to claim 1, wherein the digital signal processor classifies the pixel points of the hemangioma image into a red region and normal regions; the red region is the tumor image; by taking the largest diameter of a tumor as a diameter and a center point of the diameter as an original point a plane rectangular coordinate system is established; four normal regions having a distance of 1 cm±0.5 mm from the outer sides of the edges of the tumor in four directions of the coordinate system and having an area of 1 $cm^2$±0.5 $cm^2$ constitute the tumor side image; and the tumor side image is divided into four regions, namely a tumor side I, a tumor side II, a tumor side III and a tumor side IV (324).

5. The quantitative system according to claim 4, wherein the digital analysis software converts and outputs the tumor image and the tumor side image to red, green and blue values and an RGB value, respectively recorded as R, G, B and comprehensive RGB values; the comprehensive RGB value of the tumor image is recorded as a tumor comprehensive RGB value; and an average value of the comprehensive RGB values of the four regions, namely the tumor side I, the tumor side II, the tumor side III and the tumor side IV, of the tumor side image is calculated and then recorded as a tumor-side comprehensive RGB value.

6. The quantitative evaluation system according to claim 1, wherein the digital analysis software converts and outputs the tumor image and the tumor side image to red, green and blue values and an RGB value, respectively recorded as R, G, B and comprehensive RGB values; the comprehensive RGB value of the tumor image is recorded as a tumor comprehensive RGB value; and an average value of the comprehensive RGB values of the four regions, namely the tumor side I, the tumor side II, the tumor side III and the tumor side IV, of the tumor side image is calculated and then recorded as a tumor-side comprehensive RGB value.

7. A quantitative evaluation method for hemangioma color, wherein the quantitative evaluation method for hemangioma color is performed in the quantitative evaluation system for color of hemangioma, and the evaluation method comprises the following steps:

S1: turning on the light source device and the imaging device to perform a system stability calibration process until the system stability reaches a standard;

S2: obtaining a hemangioma image by the imaging device, and storing the hemangioma image in the storage device;

S3: dividing the hemangioma image into a tumor image and a tumor side image by the digital signal processor;

S4: calculating comprehensive RGB values of the tumor image and the tumor side image by the digital analysis software, and respectively recording results as a tumor comprehensive RGB value and a tumor-side comprehensive RGB value;

S5: calculating a therapeutic evaluation coefficient, wherein the therapeutic evaluation coefficient=tumor comprehensive RGB value-tumor-side comprehensive RGB value; and S6: displaying the hemangioma image, the tumor image, the tumor side image (32), the tumor comprehensive RGB value, the tumor-side comprehensive RGB value and the therapeutic evaluation coefficient by the display screen.

8. The quantitative evaluation method according to claim 7, wherein in S1, a distance between the imaging device and an imaging object is fixed, and the distance is 1 m.

9. The evaluation method according to claim 8, wherein a distance between the imaging device and an imaging object is fixed.

10. The quantitative evaluation method according to claim 7, wherein in S1, the system stability calibration process comprises the following steps:

S1: placing a uniform white diffuse reflection plate in a measurement region, and adjusting an aperture size of a camera or a light source box to enable one component in RGB values of the shot image to reach 255;

S2: placing a gray standard plate in the measurement region, and adjusting parameters of the camera to enable RGB three components of the output image to be 122, 122 and 121 respectively;

S3: placing a black standard plate in the measurement region and/or covering a lens cap, and adjusting the parameters of the camera to enable the RGB three components of the output image to be 0 respectively; and S4 placing a white standard plate in the measurement region, and adjusting the parameters of the camera to enable the RGB values of the output image to be 255 respectively.

11. The quantitative evaluation method according to claim 10, wherein S1, a distance between the imaging device and an imaging object is fixed, and the distance is 1 m.

12. The quantitative evaluation method according to claim 8, wherein in S3, the division of the tumor side image comprises the following steps:

S1: selecting a center of the tumor image as an original point, and equally dividing the tumor image into four quadrants by a first quadrant axis, a second quadrant axis, a third quadrant axis and a fourth quadrant axis; and S2: selecting an image having a distance of 1±0.5 cm from the outer side of the tumor image on each of the quadrant axes and having an area of 1±0.5 cm$^2$ as a tumor side image.

13. The evaluation method according to claim 7, wherein in S3, the division of the tumor side image comprises the following steps:

S1: selecting a center of the tumor image as an original point, and equally dividing the tumor image into four quadrants by a first quadrant axis, a second quadrant axis, a third quadrant axis and a fourth quadrant axis; and S2: selecting an image having a distance of 1±0.5 cm from the outer side of the tumor image on each of the quadrant axes and having an area of 1±0.5 cm$^2$ as a tumor side image.

14. The evaluation method according to claim 13, wherein the tumor side image is divided into four regions, namely a tumor side I, a tumor side II, a tumor side III and a tumor side IV.

15. The quantitative evaluation method according to claim 14, wherein in S1, a distance between the imaging device and an imaging object is fixed, and the distance is 1 m.

16. The quantitative evaluation method according to claim 13, wherein in S1, a distance between the imaging device and an imaging object is fixed, and the distance is 1 m.

17. The evaluation method according to claim 7, wherein in S3, the tumor-side comprehensive RGB value is an average value of the comprehensive RGB values of the four regions, namely the tumor side I, the tumor side II, the tumor side III and the tumor side IV, of the tumor side image.

18. The evaluation method according to claim 7, wherein the light source device comprises a light source box and a light shield; and the light source box comprises an infrared filter.

19. The quantitative evaluation method according to claim 7, wherein the digital signal processor classifies the pixel points of the hemangioma image into a red region and normal regions; the red region is the tumor image; by taking the largest diameter of a tumor as a diameter and a center point of the diameter as an original point, a plane rectangular coordinate system is established; four normal regions having a distance of 1 cm±0.5 mm from the outer sides of the edges of the tumor in four directions of the coordinate system and having an area of 1 cm$^2$±0.5 cm$^2$ constitute the tumor side image; and the tumor side image is divided into four regions, namely a tumor side I, a tumor side II, a tumor side III and a tumor side IV.

20. The quantitative evaluation method according to claim 7, wherein in S3, the division of the tumor side image comprises the following steps:

S1: selecting a center of the tumor image as an original point, and equally dividing the tumor image into four quadrants by a first quadrant axis, a second quadrant axis, a third quadrant axis and a fourth quadrant axis; and S2: selecting an image having a distance of 1±0.5 cm from the outer side of the tumor image on each of the quadrant axes and having an area of 1±0.5 cm$^2$ as a tumor side image.

* * * * *